United States Patent
Rubinstein et al.

(10) Patent No.: US 7,098,002 B1
(45) Date of Patent: Aug. 29, 2006

(54) PREPARATION OF BIOLOGICALLY ACTIVE MOLECULES

(75) Inventors: Menachem Rubinstein, Givat Shmuel (IL); Bianling Liu, Rehovot (IL); Daniela Novick, Rehovot (IL); Pierre Graber, Saint-Cergue (CH)

(73) Assignee: Yeda Research and Development Co. Ltd., (IL)

( * ) Notice: Subject to any disclaimer, the term of this patent is extended or adjusted under 35 U.S.C. 154(b) by 0 days.

(21) Appl. No.: 09/958,914

(22) PCT Filed: Apr. 13, 2000

(86) PCT No.: PCT/IL00/00220

§ 371 (c)(1),
(2), (4) Date: Feb. 26, 2002

(87) PCT Pub. No.: WO00/61768

PCT Pub. Date: Oct. 19, 2000

(30) Foreign Application Priority Data

Apr. 13, 1999 (IL) .................................... 129427

(51) Int. Cl.
*C12N 15/24* (2006.01)
*C12P 21/06* (2006.01)
*C12P 21/02* (2006.01)
*C07K 14/545* (2006.01)

(52) U.S. Cl. .................. 435/69.1; 435/69.5; 435/71.1; 435/471; 435/325; 435/252.1; 435/320.1; 530/351; 536/23.5

(58) Field of Classification Search ............... 435/69.1, 435/69.5, 71.1, 471, 325, 252.1, 320.1; 530/351, 530/387.3
See application file for complete search history.

(56) References Cited

FOREIGN PATENT DOCUMENTS

| EP | 0 646 646 | * | 4/1995 |
|----|-----------|---|--------|
| EP | 1013763 A | | 6/2000 |
| WO | WO 93/13208 | * | 7/1993 |
| WO | WO 9313208 | | 7/1993 |
| WO | WO 9724441 | | 7/1997 |
| WO | WO 9838317 | | 9/1998 |
| WO | WO 9907851 | | 2/1999 |

OTHER PUBLICATIONS

Ghayur et al. Caspase-1 processes IFN-gamma-inducing factor and regulates LPS-induced IFN-gamma production. Nature, vol. 386, Apr. 1997, pp. 619-623.*
Ushio et al, Cloning of the cDNA for Human IFN-gamma Inducing Factor Expression in *E. coli* and Studies on the Biological activities of the Protein. The Journal of Immunlogy, vol. 156, pp. 4274-4279, 1996.*
Callard et al. The Cytokine FactsBook, pp. 31-34, 1995.*
Shimpei et al. *J. Immunology*, vol. 156 (11) 4274-4279 (1996).
Yong et al., *Science*, vol. 275, (5297) 206-209 (1997).
C. Dinarello, *Cytokine and Growth Factor Reviews*, vol. 8 (4) 253-265 (Dec. 1997).

* cited by examiner

*Primary Examiner*—Eileen B. O'Hara
*Assistant Examiner*—Fozia Hamud
(74) *Attorney, Agent, or Firm*—Nixon Peabody LLP

(57) ABSTRACT

Biologically active molecules are produced from their biologically inactive precursors by mutation of their native cleavage site to a site which is capable of being cleaved by a protease, and cleavage of the mutated molecule to yield a biologically active molecule.

**

GST-Pro-LETD-hIL-18

```
    ATGGCTGCTGAACCAGTAGAAGACAATTGCATCAACTTTGTGGCAATGAAATTTATTGAC
  1 ---------+---------+---------+---------+---------+---------+ 60
    TACCGACGACTTGGTCATCTTCTGTTAACGTAGTTGAAACACCGTTACTTTAAATAACTG a   M  A  A  E  P  V  E  D  N  C  I  N  F  V  A  M  K  F  I  D    -

AATACGCTTTACTTTATAGCTGAAGATGATGAAAACCTGGAAACCGACTACTTTGGCAAG
 61 ---------+---------+---------+---------+---------+---------+ 120
    TTATGCGAAATGAAATATCGACTTCTACTACTTTTGGACCTTTGGCTGATGAAACCGTTC a   N  T  L  Y  F  I  A  E  D  D  E  N  L  E  T  D  Y  F  G  K    -

CTTGAATCTAAATTATCAGTCATAAGAAATTTGAATGACCAAGTTCTCTTCATTGACCAA
121 ---------+---------+---------+---------+---------+---------+ 180
    GAACTTAGATTTAATAGTCAGTATTCTTTAAACTTACTGGTTCAAGAGAAGTAACTGGTT a   L  E  S  K  L  S  V  I  R  N  L  N  D  Q  V  L  F  I  D  Q    -

GGAAATCGGCCTCTATTTGAAGATATGACTGATTCTGACTGTAGAGATAATGCACCCCGG
181 ---------+---------+---------+---------+---------+---------+ 240
    CCTTTAGCCGGAGATAAACTTCTATACTGACTAAGACTGACATCTCTATTACGTGGGGCC a   G  N  R  P  L  F  E  D  M  T  D  S  D  C  R  D  N  A  P  R    -

ACCATATTTATTATAAGTATGTATAAAGATAGCCAGCCTAGAGGTATGGCTGTAACTATC
241 ---------+---------+---------+---------+---------+---------+ 300
    TGGTATAAATAATATTCATACATATTTCTATCGGTCGGATCTCCATACCGACATTGATAG a   T  I  F  I  I  S  M  Y  K  D  S  Q  P  R  G  M  A  V  T  I    -
```

Fig. 8 (a)

```
    TCTGTGAAGTGTGAGAAAATTTCAACTCTCTCCTGTGAGAACAAAATTATTTCCTTTAAG
301 ---------+---------+---------+---------+---------+---------+ 360
    AGACACTTCACACTCTTTTAAAGTTGAGAGAGGACACTCTTGTTTTAATAAAGGAAATTC a    S  V  K  C  E  K  I  S  T  L  S  C  E  N  K  I  I  S  F  K    -

GAAATGAATCCTCCTGATAACATCAAGGATACAAAAAGTGACATCATATTCTTTCAGAGA
361 ---------+---------+---------+---------+---------+---------+ 420
    CTTTACTTAGGAGGACTATTGTAGTTCCTATGTTTTTCACTGTAGTATAAGAAAGTCTCT a    E  M  N  P  P  D  N  I  K  D  T  K  S  D  I  I  F  F  Q  R    -

AGTGTCCCAGGACATGATAATAAGATGCAATTTGAATCTTCATCATACGAAGGATACTTT
421 ---------+---------+---------+---------+---------+---------+ 480
    TCACAGGGTCCTGTACTATTATTCTACGTTAAACTTAGAAGTAGTATGCTTCCTATGAAA a    S  V  P  G  H  D  N  K  M  Q  F  E  S  S  S  Y  E  G  Y  F    -

CTAGCTTGTGAAAAAGAGAGAGACCTTTTTAAACTCATTTTGAAAAAGAGGATGAATTG
481 ---------+---------+---------+---------+---------+---------+ 540
    GATCGAACACTTTTTCTCTCTCTGGAAAAATTTGAGTAAAACTTTTTCTCCTACTTAAC a    L  A  C  E  K  E  R  D  L  F  K  L  I  L  K  K  E  D  E  L    -

GGGGATAGATCTATAATGTTCACTGTTCAAAACGAAGACTAG
541 ---------+---------+---------+---------+-- 582
    CCCCTATCTAGATATTACAAGTGACAAGTTTTGCTTCTGATC a    G  D  R  S  I  M  F  T  V  Q  N  E  D  *    -
```

Fig. 8 (b)

PREPARATION OF BIOLOGICALLY ACTIVE MOLECULES

CROSS-REFERENCE TO RELATED APPLICATIONS

This application is a 371 National Phase Entry Application of co-pending International Application PCT/IL00/00220, filed Apr. 13, 2000, which designated the U.S. and was published in English, and which claims the benefit under 35 U.S.C. § 119 of Israeli Patent Application No. 129427, filed April 13, 1999.

FIELD OF THE INVENTION

The present invention in general relates to the production of biologically active molecules which occur as inactive precursors and which are cleaved in vivo by proteases into mature, biologically active molecules.

More specifically, the invention relates to the production of caspases and cytokines, which are produced in vivo from their corresponding precursors by autocleavage, cleavage by other caspases or by cleavage, e.g. with the protease caspase-1, also known as interleukin-1 converting enzyme (ICE). Examples of cytokines produced in such a manner are interleukin-1β and interleukin-18.

BACKGROUND OF THE INVENTION

Caspases are a family of cysteine proteases that cleave their target protein following an Asp residue. Of the eleven published known caspases, caspase-1, and probably caspases-4, -5, and -11 seem primarily involved in the processing of proinflammatory cytokines, whereas others play crucial roles in the initiation and execution of apoptosis or programmed cell death. Caspases share several common features among them that they are synthesized as catalytically inactive zymogens that are generally activated by cleavage after specific internal Asp residues present in interdomain linkers and the ability to cleave their substrates after Asp residues. As a result certain mature active caspases, in particular those that are derived from the long prodomain caspases can process and activate their own and other inactive caspase zymogens. On the basis of primary structure, proapoptotic caspases can be divided into two classes, class I including caspase-2, -8, -9, and -10 that contain a long amino-terminal prodomain, and class II such as caspase-3, -6, and -7 with a short or absent prodomain. In vitro cleavage experiments suggest that class II caspases require activated class I caspases for their proteolytic processing (12).

Another classification of caspases is by the specificity of the cleave site (13). Here Group 1 caspases have the consensus sequence WEHD (SEQ ID NO: 15) (caspases-1, -4, and -5), Group II caspases the consensus sequence DExD (caspases-2, -3 and -7), and Group III caspases the consensus sequence (IVL)ExD (caspases-6, -8 and -9). The caspase-8 optimal site is LETD (SEQ ID NO: 16) (14).

Interleukin 18 (IL-18), initially described as an interferon-γ (IFN-γ)-inducing factor is a recently characterized cytokine that shares structural features with the IL-1 family of proteins (1–4). IL-18 was initially purified and subsequently cloned from the liver of mice treated with heat-inactivated *Propionbacterium acnes* (*P. acnes*) followed by lipopolysaccharide (LPS) (2,5). Cloning of human IL-18 has also been recently described (3).

Like IL-12, IL-18 is produced by activated macrophages such as liver Kupffer cells and other resident macrophages (3). IL-18 is an early inducer of the Th1 response, co-stimulating the production of IFN-γ, as well as TNF-γ, granulocyte-macrophage colony-stimulating factor and IL-2 (6). In addition, it potentiates anti-CD3-induced T-cell proliferation and increases natural killer cell cytotoxicity by augmenting the expression of Fas Ligand (6,7).

Unlike most other cytokines, which exhibit a four-helix bundle structure, IL-18 and IL-1β have an all β-pleated sheet structure (7). Similarly to IL-1β, IL-18 is synthesized as a biologically inactive precursor (proIL-18), lacking a signal peptide (3). The IL-1β and IL-18 precursors are cleaved by caspase 1 (IL-1β-converting enzyme, or ICE), that cleaves after an aspartic acid residue in the P1 position. The resulting mature cytokines are readily released from the cell (8,9). Studies with caspase-1-deficient mice demonstrated the important role of mature IL-18 as an inducer of IFN-γ and Th1 responses. Injection of such mice with *P. acnes* and LPS resulted in low levels of circulating IFN-γ compared with wild-type mice (8,9). Injection of IL-18 restored the LPS-induced IFN-γ level in the caspase-1-deficient mice (9), further supporting the concept that caspase-1 is involved in the production of active IL-18. Other caspases and particularly those cleaving intracellular proteins associated with apoptosis were at least 100-fold less active than caspase-1 (9). Similar studies with IL-18-deficient mice revealed its role in NK cell activity and cytokine induction (10).

Recombinant IL-1β and mouse IL-18 expressed in *E. coli* may be refolded to produce a fully active cytokine. Attempts to express the mature form of human IL-18 in *E. coli* or other hosts did not provide a fully active cytokine. Because of its potential therapeutic uses, e.g. in malignancies, or in any condition in which induction of interferon-γ production is wanted, it is desired to establish an efficient expression system for the production of mature biologically active human IL-18.

SUMMARY OF THE INVENTION

The present invention allows the production of molecules which, in their natural process of formation are produced in a biologically inactive precursor form, and become active after cleavage of their precursor. This cannot be easily accomplished in vitro.

The present invention thus provides a method for the production of a biologically active molecule from its biologically inactive precursor by mutation of its natural cleavage site to a site susceptible to cleavage by a common protease, and cleaving the mutated molecule to yield a biologically active molecule.

Preferably, the biologically active molecule is a caspase or a cytokine, more preferably selected from IL-1β and IL-18.

In such cytokines the natural cleavage site preferred is a caspase-1 cleavage site.

The common protease employed for cleavage may be selected from thrombin, enterokinase, subtilisin, genenase™ (New England Biolabs, Beverly Mass., USA), the human rhinovirus 3C protease and Factor Xa protease. When a caspase is employed for cleavage, caspase-8 is preferred.

In a preferred embodiment of the present invention, the method comprises transfecting a host with a vector comprising a cDNA encoding a precursor of a biologically active molecule mutated at its cleavage site, culturing the transfected host, expressing the precursor and isolating the biologically active molecule after treatment with a protease.

Optionally this may be accomplished in that the cDNA is fused in frame past a glutathione-S-transferase (GST) coding sequence and the expressed fusion molecule is captured on glutathione agarose beads prior to treatment with the protease.

The present invention also provides a cDNA encoding a mutated precursor of a biologically active molecule, optionally fused to a GST coding sequence.

In one embodiment of the present invention there is provided a process of producing and/or purifying a recombinant hybrid polypeptide or fusion protein. More specifically, a DNA fragment coding for a protein molecule is fused to a DNA fragment coding for a binding protein using, as linking sequence, the DNA coding for a peptide sequence which is recognized and cut by a caspase. The fused DNA is inserted into a cloning vector which is used to transform an appropriate host. Upon expression, the hybrid polypeptide is purified by contacting it with a ligand or substrate to which the binding protein has specific affinity, e.g. by affinity chromatography.

In a preferred embodiment of the present invention, the binding protein is GST and the cleavage site is the caspase-8 cleavage site The invention also relates to biologically active molecules prepared with the above method.

Expression of mature IL-18 in *E. coli* results in a protein lacking biological activity. Attempts to correctly refold the IL-18 polypeptide backbone of IL-18 expressed in *E. coli* were so far unsuccessful. Human IL-18 and human IL-1β are expressed in vivo as proIL-18 and proIL-1β precursors, which are cleaved by caspase-1 to yield biologically active mature IL-18 and IL-1β, respectively. However, caspase-1 is not available commercially. The present invention provides a simple procedure for production in *E. coli* of a biologically active molecule, in particular a cytokine and more particular, human IL-18. For this purpose, a cDNA encoding human proIL-18 was constructed in which the caspase-1 cleavage site was mutated into the cleavage site of a commercially available protease, e.g., factor Xa. For ease of manipulation, the mutated proIL-18 cDNA was fused to a glutathione-S-transferase (GST) coding sequence. The resulting GST-proIL-18 fusion protein, having a factor Xa cleavage site was expressed in *E. coli* and captured on glutathione agarose beads. Mature human IL-18, exhibiting high biological activity was released from the beads by cleavage with Factor Xa.

Similarly, the DNA sequence coding for the caspase-1 cleavage site of human IL-1β is mutated into a cleavage site of factor Xa. For ease of manipulation, the mutated proIL-1β cDNA is fused in frame to a glutathione-S-transferase (GST) coding sequence. The resulting GST-proIL-1β fusion protein, having a factor Xa cleavage site is expressed in *E. coli* and captured on glutathione agarose beads. Mature human IL-1β is released from the beads by cleavage with Factor Xa.

When caspase-8 is employed for cleavage, a similar procedure is carried out, the difference being that the caspase-1 cleavage site of either human IL-18 or human IL-1β is mutated into a cleavage site of caspase-8. Thereafter fusion to a GST coding sequence and further method steps are carried out as described above.

BRIEF DESCRIPTION OF THE FIGURES

FIG. 8 shows the sequence of the GST-pro-hIL-18$_{LETD}$. The box indicates the Caspase-8 cleavage site. The underlined sequence is the mature hIL-18.

DETAILED DESCRIPTION OF THE INVENTION

Figure 1:
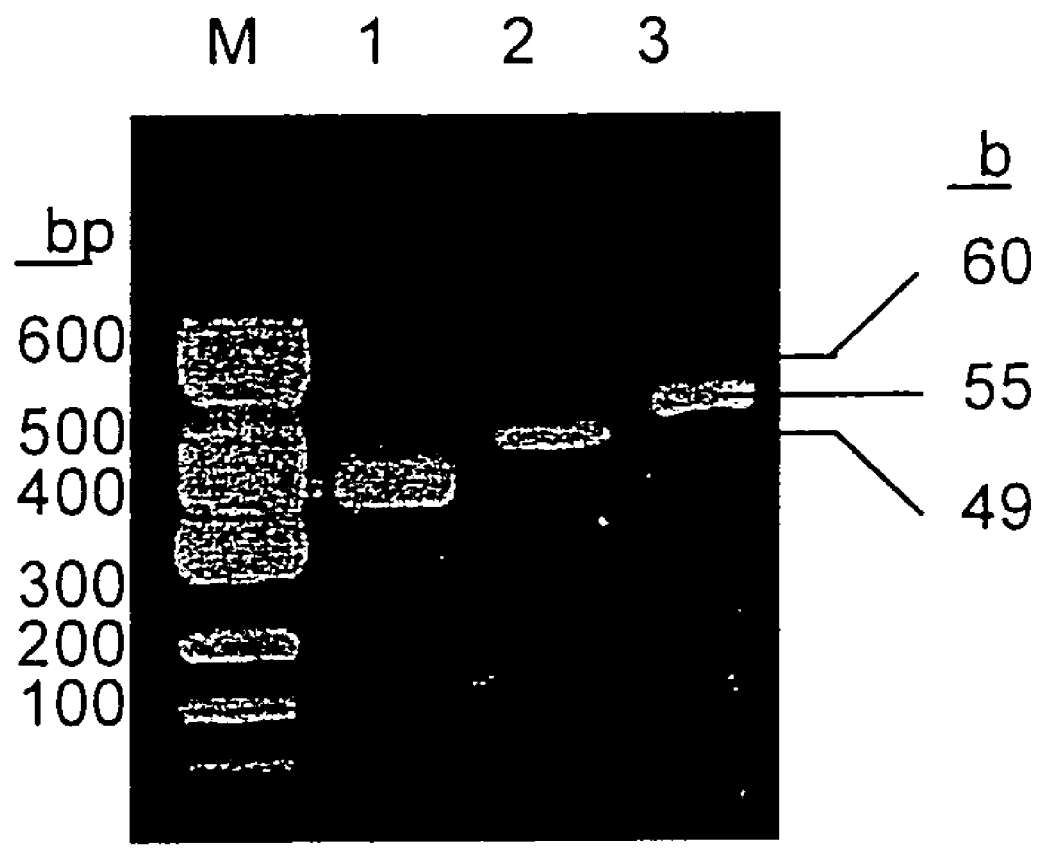
FIG. 1 describes the cloning of cDNA encoding human proIL-18 mutant (proIL-18$_{IEGR}$). This cDNA was cloned by three steps of PCR using an overlapping primer method. The lanes are: M, DNA size markers, indicated on the left side; 1, a 498 bp DNA produced by the first PCR; 2, a 551 bp DNA produced by the second PCR; 3, a 600 bp DNA produced by the third PCR, encoding human proIL-18$_{IEGR}$.

According to the present invention, a cDNA encoding human proIL-18 in which the Caspase-1 cleavage site was mutated into a Factor Xa site, was prepared. Other mutations, generating cleavage sites suitable for other proteases may be used.

Examples of possible cleavage sites and suitable proteases include:

Leu-Val-Pro-Arg-Gly-Ser (SEQ ID NO:1), a sequence cleaved between the amino acids Arg and Gly by the protease Thrombin.

Ile-Glu-Gly-Arg-(SEQ ID NO:2), a sequence cleaved after the Arg residue by the protease Factor Xa.

Asp-Asp-Asp-Lys-(SEQ ID NO:3), a sequence cleaved after the Lys residue by the protease Enterokinase.

His-Tyr-(SEQ ID NO:4), a sequence cleaved after the Tyr residue by the protease subtilisin or by its variant Genenase™ (New England Biolabs).

Tyr-His (SEQ ID NO:5), a sequence cleaved after the Tyr residue by the protease subtilisin or by its variant Genenase™ (New England Biolabs).

Leu-Glu-Val-Leu-Phe-Gln-Gly-Pro (SEQ ID NO:6), a sequence cleaved after the Gln residue by the human rhinovirus 3C protease.

Similarly, a cDNA encoding human proIL-1β in which the Caspase-1 cleavage site is mutated into a Factor Xa site is prepared. Other mutations, generating cleavage sites suitable for other proteases may be used.

Examples of possible cleavage sites and suitable proteases include:

Ile-Glu-Gly-Arg-(SEQ ID NO:2), a sequence cleaved after the Arg residue by the protease Factor Xa.

Asp-Asp-Asp-Lys-(SEQ ID NO:3), a sequence cleaved after the Lys residue by the protease Enterokinase.

Leu-Glu-Val-Leu-Phe-Gln-Gly-Pro (SEQ ID NO:6), a sequence cleaved after the Gln residue by the human rhinovirus 3C protease.

The choice of mutation depends on the following parameters: the cleavage site generated by the mutation must be very specific to avoid undesired cleavages at other sites within the polypeptide backbone of the proIL-18 or proIL-1β; the protease must exhibit a high level of specificity for the engineered cleavage site; the protease must be conveniently available, e.g., from commercial sources; and the mutation preferably should not introduce a major alteration in the secondary or tertiary structure of the proIL-18 or proIL-1β. The use of Factor Xa or Enterokinase or subtilisin is preferable over the other proteases because the resulting IL-18 or IL-1β has no mutated amino acid. The use of Factor Xa is most favorable because it requires the most conservative mutations, thereby reducing the risk of altered secondary or tertiary structure of the proIL-18 or proIL-1β and the risk that cleavage will not take place. The use of Factor Xa or Enterokinase is preferable over the other proteases because the resulting IL-18 or IL-1β have no mutated amino acids.

In order to construct a cDNA encoding a human proIL-18 mutant (proIL-18$_{IEGR}$) in which the Caspase-1 cleavage site is mutated into a Factor Xa cleavage site, the following mutations were introduced in the human proIL-18 cDNA: L33I; S35G and D36R. These mutations yielded the Factor Xa recognition sequence IEGR.

Figure 2:
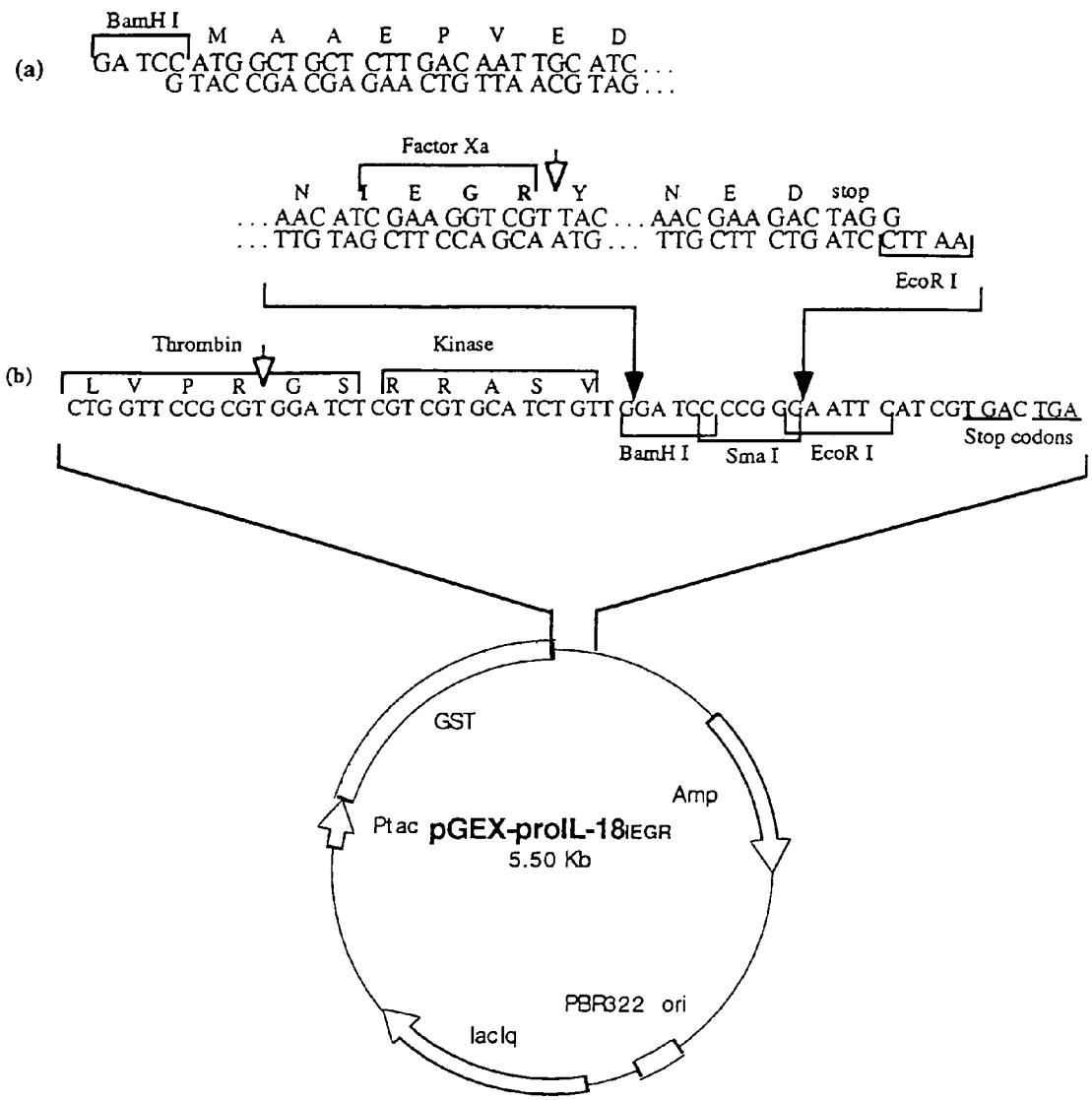
FIG. 2 shows the structure of the expression plasmid pGEX-proIL-18$_{IEGR}$. (a) Flanking nucleic acid sequences of the 600 bp BamH I/EcoR I cDNA encoding human proIL-18$_{IEGR}$. Restriction sites for BamH I and EcoR I and the target site for Factor Xa are indicated by brackets. An open arrow indicates the Factor Xa cleavage site. (b) Schematic representation of pGEX-2TK. The restriction sites are also shown. The filled arrow indicates the BamH I/EcoR I ligation site of the insert.

A vector expressing human proIL-18$_{IEGR}$ was constructed in the following manner. Peripheral blood mononuclear cells (PBMC) of a healthy donor were stimulated by bacterial lipopolysaccharide (LPS). Total RNA was extracted from the cells. The RNA was reverse-transcribed and the resulting cDNA served as a template for polymerase chain reaction (PCR). The mutation in the sequence was introduced using overlapping primers in three steps of PCR (FIG. 1). The resulting 600 bp PCR product, coding for mutated human proIL-18 was cloned into a TA cloning vector (pGEM-T easy, Promega) and its DNA sequence was verified by DNA sequence analysis. The resulting pGEM-T-proIL-18$_{IEGR}$ plasmid was cut-by EcoR I and BamH I and the 600 bp fragment encoding human proIL-18$_{IEGR}$ was subcloned into the prokaryotic expression vector pGEX-2TK containing the GST gene sequence (Pharmacia). The resulting expression vector contained the sequence of the human proIL-18$_{IEGR}$ gene fused in frame to the 3' end of the GST gene (FIG. 2).

Figure 3:
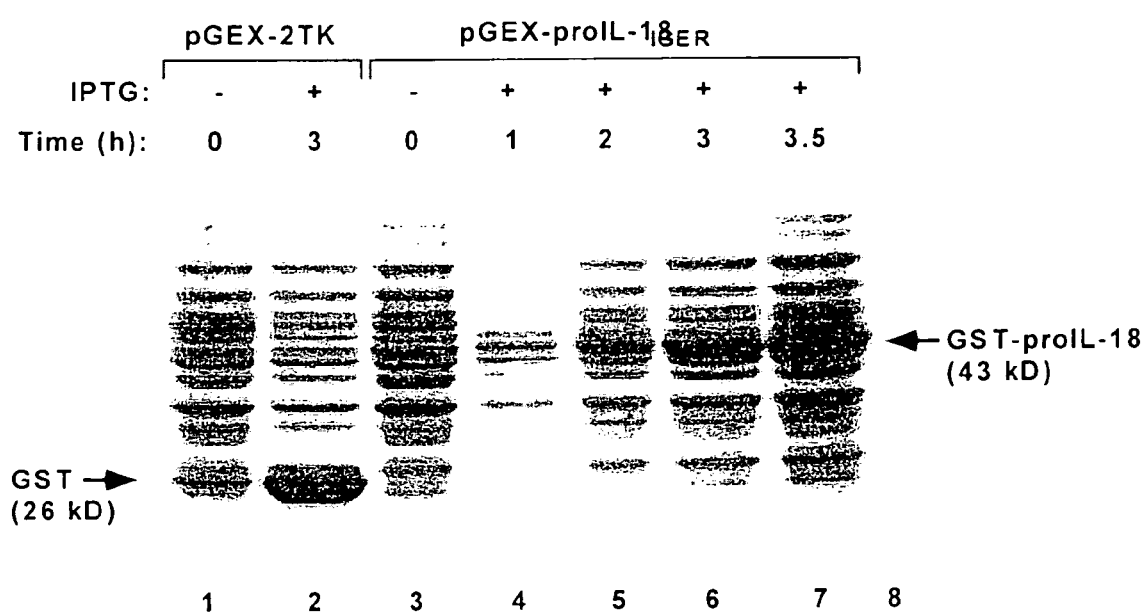
FIG. 3 shows SDS-PAGE of crude protein extracts of *E. coli* expressing the GST-proIL-18$_{IEGR}$ fusion protein. The lanes are: 1. Cells transformed with the parental plasmid pGEX-2TK without induction. 2. Cells transformed with the parental plasmid pGEX-2TK and induced with 0.1 mM isopropylthio galactoside (IPTG). The expected 26 kD band of glutathione thioreductase (GST) is indicated by an arrow on the left side. Lanes 3–7 show cells transformed with plasmid pGEX-proIL-18$_{IEGR}$ and either not induced (lane 3) or induced with IPTG for the indicated times. The 43 kD band indicated by an arrow on the right side corresponds in size to the GST-proIL-18$_{IEGR}$ fusion protein.
Figure 4:
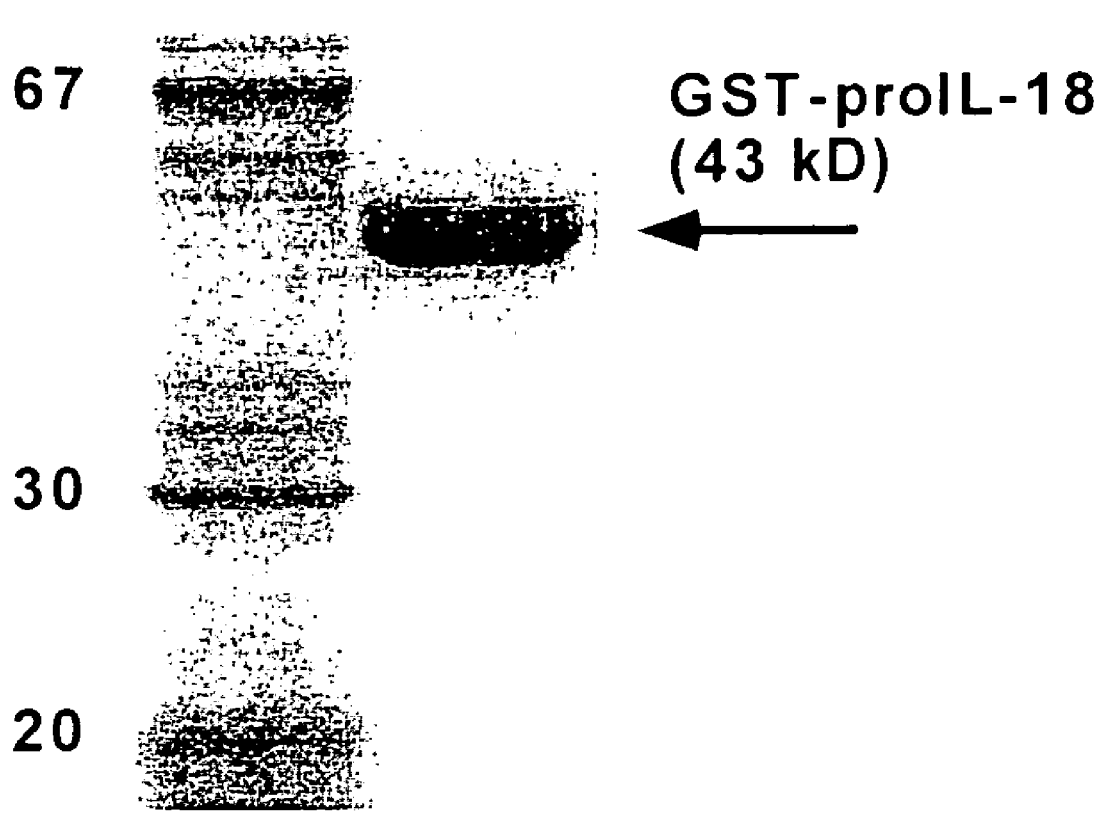
FIG. 4 shows SDS-PAGE (10% acrylamide) of the GST-proIL-18$_{IEGR}$ fusion protein following purification on glutathione-agarose. Supernatant of bacterial sonicate (see FIG. 3 lane 7) was affinity-purified on glutathione agarose. The lanes are: 1. Molecular mass markers (indicated by kD on the left side); 2. Affinity-purified GST-proIL-18$_{IEGR}$. The gel was stained with Coomassie blue.
Figure 5:
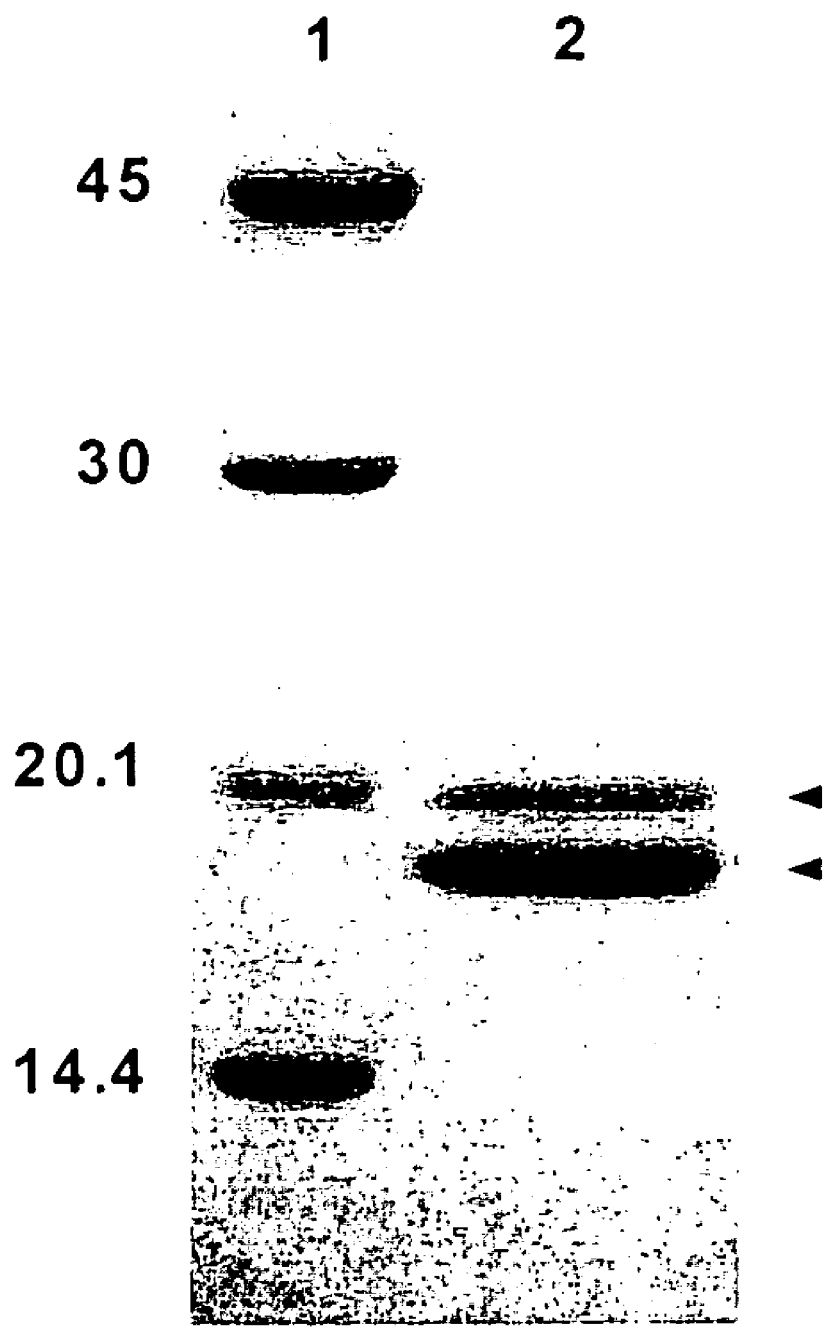
FIG. 5 shows SDS-PAGE (12% acrylamide) of the purified human IL-18. GST-proIL-18$_{IEGR}$ fusion protein captured on glutathione agarose beads and incubated with Factor Xa at a protease to substrate ratio 1:50 (w/w) and the supernatant was analyzed after 6 h. Lane 1, molecular weight markers, indicated in kD on the left side; lane 2. Human IL-18 in the supernatant of the glutathione-agarose beads. The gel was stained with Coomassie blue.

Expression and purification of GST-proIL-18$_{IEGR}$ was then performed. A fresh single colony of *E. coli* JM109 transformed with plasmid pGEX-proIL-18$_{IEGR}$ was grown with shaking at 37° C., until reaching a density of 0.6 OD$_{600}$. Protein expression was then induced by isopropyl-thiogalactoside (IPTG) and further culturing at 37° C. for 3 h. SDS-PAGE of total bacterial proteins revealed the induction of a 43 kD protein, corresponding in size to GST-proIL-18$_{IEGR}$ (FIG. 3). All downstream steps for isolation of the GST-proIL-18$_{IEGR}$ were carried out at 4° C. Bacteria were harvested by centrifugation, resuspended in phosphate buffered saline (PBS), containing protease inhibitors. The bacteria were lysed by sonication, Triton X-100 was added to a final concentration of 1% and the clarified lysate was mixed with glutathione-agarose beads (Pharmacia). The beads were washed and an aliquot of the beads was analyzed by SDS-PAGE. A single 43 kD band, corresponding to the GST-proIL-18$_{IEGR}$ fusion protein was found (FIG. 4). The beads were then digested with Factor Xa and the supernatant was collected. SDS-PAGE of the supernatant gave a major band of approximately 18 kD, in agreement with the expected mass of mature human IL-18. An additional weaker band of 19.5 kD was seen as well (FIG. 5). Protein sequence analysis of the 18 kD and the 19.5 kD bands gave in both cases the expected N-terminal sequence of mature human IL-18. A 43 kD band, corresponding to the GST-proIL-18$_{IEGR}$ fusion protein was still present in the glutathione-agarose beads following digestion, indicating an incomplete cleavage (not shown).

Figure 6:
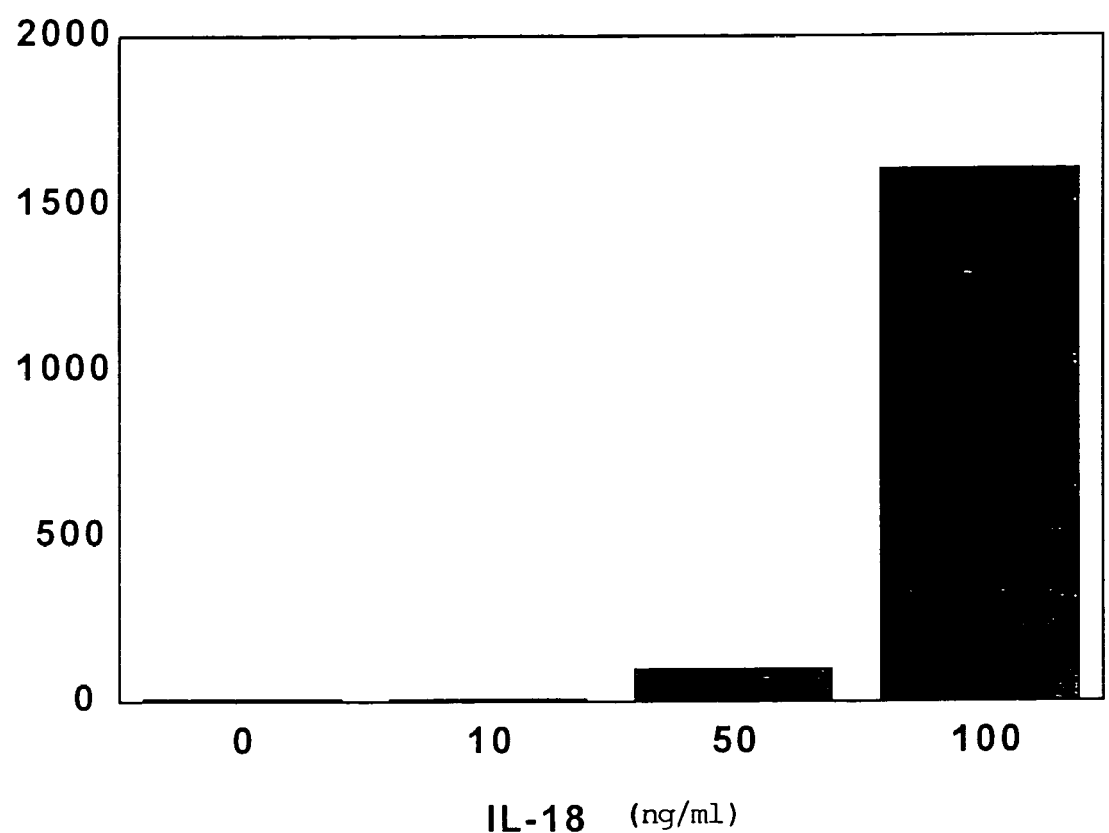
FIG. 6 shows a bioassay of the human IL-18. Human IL-18 at the indicated doses was added to the cultures of murine plastic-nonadherent spleen cells ($5 \times 10^6$ cells/well) in the presence of Concanavalin A (0.125 μg/ml) and polymyxin B (1 μg/ml). The supernatant was assayed for murine interferon-gamma by ELISA. The level of interferon-gamma induced by IL-18 (100 ng/ml) in the absence of Con A was 160 pg/ml.

The recombinant human IL-18 was assayed for biological activity in murine splenocytes, based on its ability to induce the expression of interferon-gamma. Incubation of mouse non-adherent spleen cells with human IL-18 alone showed little IFN-gamma production, suggesting a requirement for a co-stimulant. Con A alone at 0.125 µg/ml failed to induce significant levels of IFN-γ. When the non-adherent splenocytes were incubated with Con A and IL-18 of the present invention, a dose-dependent induction of IFN-γ was obtained (FIG. 6).

In order to construct a cDNA encoding a human proIL-1β mutant (proIL-1β$_{IEGR}$) in which the Caspase-1 cleavage site is mutated into a Factor Xa cleavage site, the following mutations are introduced in the human proIL-1β cDNA: Y113I, V114E, H115G and D116R. These mutations yield the Factor Xa recognition sequence IEGR.

The following steps are taken in order to construct a vector expressing human proIL-1β$_{IEGR}$. Peripheral blood mononuclear cells (PBMC) of a healthy donor are stimulated by bacterial lipopolysaccharide (LPS). Total RNA is extracted from the cells. The RNA is reverse-transcribed and the resulting cDNA serves as a template for polymerase chain reaction (PCR) with primers corresponding to the coding sequence of human proIL-1β. The resulting PCR product is cloned into a TA cloning vector, e.g., pGEM-T easy from Promega, and then subjected to site-directed mutagenesis with a suitable oligonucleotide. The sequence of the resulting vector, coding for mutated human proIL-1β, is verified by sequence analysis. The resulting pGEM-T-proIL-1β$_{IEGR}$ plasmid is cut by proper restriction enzymes and the ~820 bp fragment encoding human proIL-1β$_{IEGR}$ is subcloned into the prokaryotic expression vector pGEX-2TK (Pharmacia). The resulting expression vector contains the sequence of the human proIL-1β$_{IEGR}$ gene fused in frame to the 3' end of the GST gene.

Expression and purification of GST-proIL-1β$_{IEGR}$ is similarly performed. A fresh single colony of E. coli JM109 transformed with plasmid pGEX-proIL-1β$_{IEGR}$ is grown with shaking at 37° C., until reaching a density of 0.6 OD$_{600}$. Protein expression is then induced by isopropyl-thiogalactoside (IPTG) and further culturing at 37° C. for 3 h. SDS-PAGE of total bacterial proteins reveals the induction of a ~52 kD protein, corresponding in size to GST-proIL-1β$_{IEGR}$. All downstream steps for isolation of the GST-proIL-1β$_{IEGR}$ are carried out at 4° C. Bacteria are harvested by centrifugation, resuspended in phosphate buffered saline (PBS), containing protease inhibitors. The bacteria are lysed by sonication, Triton X-100 is added to a final concentration of 1% and the clarified lysate is mixed with glutathione-agarose beads (Pharmacia). The beads are washed and an aliquot of the beads is analyzed by SDS-PAGE for the presence of the ~52 kD GST-IL-1β fusion protein. The beads are then digested with Factor Xa and the supernatant containing mature human IL-1β is collected.

In another embodiment of the present invention, the expression and purification of a polypeptide is obtained by producing a fusion protein having the cleavage site for a caspase. A plasmid expressing a binding peptide fused to a protein of interest can be mutated so that a Caspase cleavage site is introduced in a position convenient for the purification of an active polypeptide.

Figure 7:
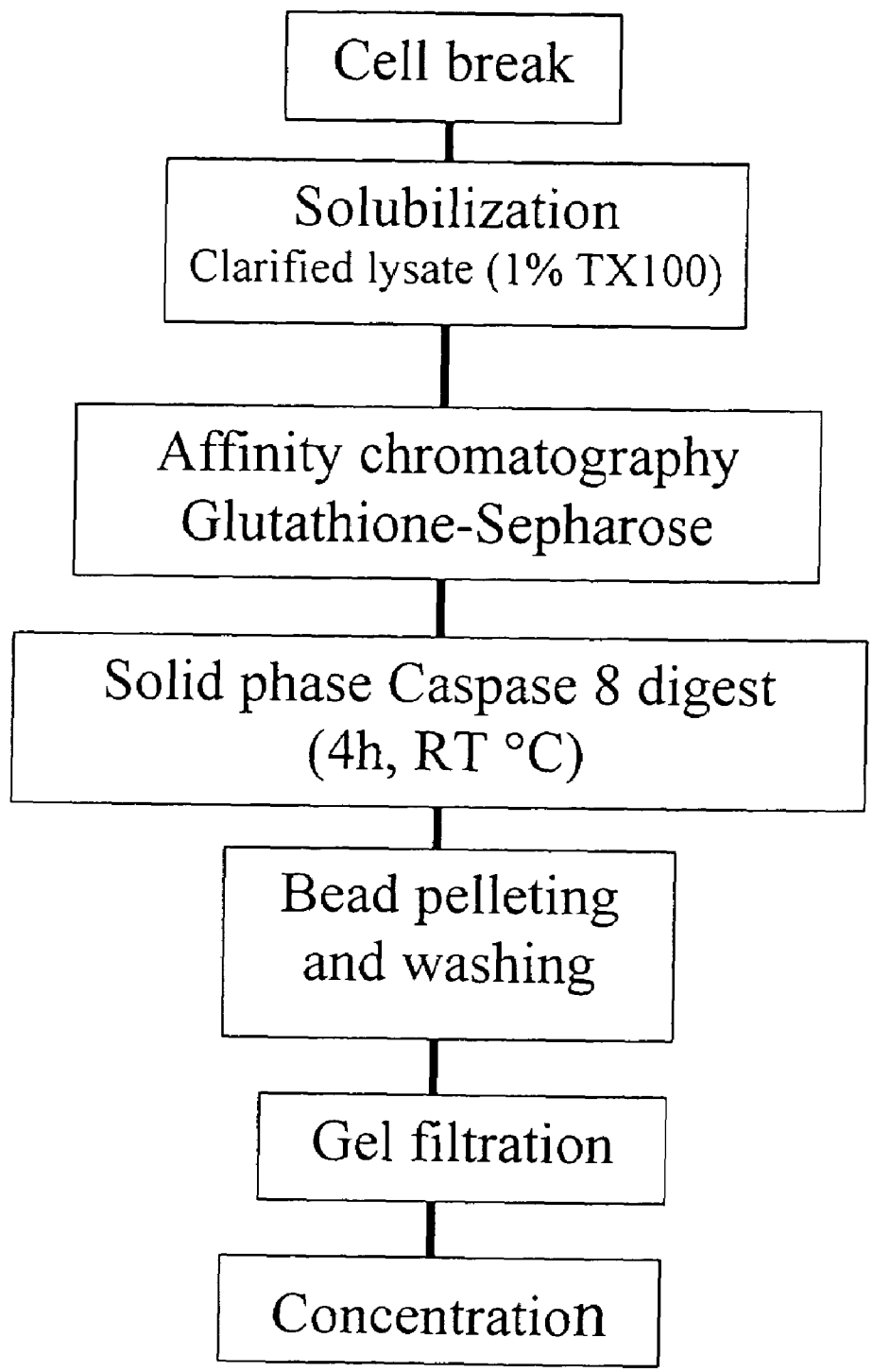
FIG. 7 shows the basic procedure for the purification of hIL-18 using Caspase-8 in schematic form.

Caspase recognition sites are composed of 4 amino acids, the last one being an aspartic acid. Generally, caspases show an higher and different specificity for the cleavage sites than commonly used proteases, offering significant advantages towards proteases previously described as useful for cutting fusion peptides. The purification procedure is examplified in FIG. 7.

Preferred cleavage sites for each caspase are described in literature (Ann Rev. Biochem, 1999, 68:383–424). All of them have the residue Asp in common in the PI position.

The plasmid described above, pGEX-proIL-18$_{IEGR}$, was modified to obtain a different human proIL-18 mutant (proIL-18$_{LETD}$, see FIG. 8) in which the Factor Xa cleavage site is mutated into a caspase-8 cleavage site. This allows the use of caspase-8 for cleavage.

Another advantage of using a caspase is their high efficiency, in terms of digestion yield and digestion time. It was found that when comparing the IL-18 protein obtained from pGEX-proIL-18IEGR and pGEX-proIL-18LETD, the amount of enzyme and the time needed to obtain 1 mg of hIL-18 is reduced. The procedure lead to the production of a protein of the expected size (FIG. 9) and bioactivity.

Caspase-8 is not the only suitable caspase and, according to the presence or absence of a specific caspase cleavage site in a protein of interest to purify or any other criteria, the mutations corresponding to the cleavage site of any other caspase can be used.

The caspase can be removed from the protein of interest using standard purification methods, such as e.g. gel filtration or ion-exchange chromatography.

In conclusion, the method described here provides purified, biologically active human proteins, such as IL-18 and IL-1β from E. coli. It appears that correct folding of these cytokines requires expression as a precursor first, and then cleavage to its mature form.

Human IL-18 differs in this respect from murine IL-18, which may be expressed in host cells as a mature, biologically active cytokine.

The invention will now be illustrated by the following non-limiting examples:

EXAMPLE 1

Construction of a Plasmid Coding for Human Pro IL-18 with a Factor Xa Site

PBMC were obtained from peripheral blood of a healthy volunteer by Ficoll-Paque PLUS (Pharmacia) density gradient separation. The PBMC were washed twice with ice-cold PBS containing 2% FBS and resuspended at $2.5 \times 10^6$ cells/ml in RPMI-1640 medium, supplemented with fetal bovine serum (FBS), 2 mM L-glutamine, 100 U/ml penicillin and 100 U/ml streptomycin (RPMI-10). The culture was stimulated with LPS (1 µg/ml, 3 h, 37° C.). Total RNA was extracted from the cells with the TriPure™ Isolation Reagent (Boehringer Mannheim). One µg total RNA was used for RT-PCR with the Titan one tube RT-PCR kit (Boehringer Mannheim) according to the manufacturer's instructions.

ProIL-18$_{IEGR}$ cDNA was constructed by a three-step PCR, using the overlapping primer method. The various primers were designed on the basis of the human proIL-18 cDNA (GenBank accession no. D49950, (3)).

For the first PCR, the forward primer was:

5'-AACATCGAAGGTCGTTACTTTGGCAAGCTTGA-ATC-3', (SEQ ID NO:7) and the reverse primer was 5'-CGC-GAATTCCTAGTCTTCGTTTTGAACAGT-3' (SEQ ID NO:8). An Eco RI site was included in the reverse primer. The template was a reverse-transcribed total cellular RNA, isolated from the LPS-stimulated PBMC. The thermocycle conditions were: 10 cycles of 94° C., 30 sec; 55° C., 30 sec and 68° C., 2 min followed by 25 cycles of 94° C., 30 sec; 55° C., 30 sec and 68° C., 125 sec/cycle. The resulting 498 bp PCR product was amplified in the second PCR step using the overlapping forward primer:

5'-TGGCAATGAAATTTATTGACAATACGCTTTAC-TTTATAGCTGAAGATGATGAAAACATC-GAAGGTCGTTACTTTG-3' (SEQ ID NO:9), and the reverse primer of the previous step. The thermocycling conditions were: 30 cycles of 94° C., 30 sec; 56° C., 30 sec and 72° C., 1 min. The resulting 551 bp product was amplified in the third step using the overlapping forward primer:

5'-CGTGGATCCATGGCTGCTGAACCAGTA-GAAGACAATTGCATCAACTTTGTGG CAATGAAATT-TATTGAC-3' (SEQ ID NO:10) and the reverse primer of the previous steps. A BamH I site was included in the forward primer. The thermocycling conditions were the same as those of the previous step. The resulting 0.6 kb PCR product (FIG. 1) was purified by a High Pure™ PCR product purification kit (Boehringer Mannheim) and ligated into the pGEM-T Easy vector to yield plasmid pGEM-proIL-18$_{IEGR}$. Ligation products were transformed into JM109 competent cells (Promega Corporation). Standard cloning protocols were used throughout (11).

Plasmid pGEM-proIL-18$_{IEGR}$ from a single colony was verified for the presence of a correct insert by restriction enzyme digestion and DNA sequencing. The plasmid was digested with BamH I and EcoR I. The resulting BamH I/EcoR I DNA encoding human proIL-18$_{IEGR}$ was resolved by electrophoresis in 1.0% agarose and the 0.6 kb band was isolated from the gel by a QIAquick Gel Extraction Kit (DIAGEN, Germany). This DNA was ligated into the pGEX-2TK expression vector (Pharmacia) which was linearized with BamH I and EcoR I. The resulting recombinant plasmid pGEX-proIL-18$_{IEGR}$ (FIG. 2) was transformed into *E. coli* JM109 strain and the resulting vector was confirmed by restriction enzyme digestion and nucleic acid sequencing.

EXAMPLE 2

Expression and Purification of GST-proIL-18$_{IEGR}$ Fusion Protein

A 50 ml overnight culture from a fresh single colony of *E. coli* JM109 transformed with plasmid pGEX-proIL-18$_{IEGR}$ was diluted in 450 ml LB medium containing 100 U/ml ampicillin and grown with shaking at 37° C., until reaching a density of 0.6 OD$_{600}$. Protein expression was then induced by adding IPTG to a final concentration of 0.1 mM and further culturing at 37° C. for 3 h. Bacteria were harvested by centrifugation (5,000×g, 5 min, 4° C.) and rapidly resuspended in a 1:100 starting volume of ice-cold phosphate buffered saline (PBS; 150 mM NaCl, 16 mM Na2HPO4, 4 mM NaH2PO4, pH 7.3), containing the protease inhibitors (leupeptin 1 µg/ml, pepstatin A 1 µg/ml, aprotinin 2 µg/ml, PMSF 0.2 mM and EDTA 5 mM). Cells were lysed on ice by mild sonication (4×15 sec bursts). Triton X-100 was added to a final concentration of 1% and the mixture kept on ice for 5 min. The clarified lysate (14,000×g, 15 min, 4° C.) was mixed with a 50% suspension of glutathione-agarose beads (2 ml, Pharmacia) and the mixture was incubated with mild shaking at 4° C. for 3 h. The beads were pelleted by centrifugation (500×g, 5 min), washed twice with 10 volumes of lysis buffer (1% Triton X-100 in PBS), twice with 10 volumes of 20 mM Tris-HCl, pH 8.0, twice with 10 volumes of 20 mM Tris-HCl, pH 8.0, 150 mM NaCl, and twice with 10 volumes of 20 mM Tris-HCl, pH 8.0, 150 mM NaCl, 2.0 mM CaCl2 (Cleavage Buffer). All steps were carried out at 4° C.

EXAMPLE 3

Cleavage of the Fusion Protein and Purification of Mature Human IL-18

The glutathione-agarose beads with bound GST-proIL-18$_{IEGR}$ fusion protein were incubated (6 h, 23° C.) with Factor Xa (New England Biolabs) in 1 ml Cleavage Buffer, using a protease to substrate ratio of 1:50 (w/w), with constant mixing on a rotating wheel. This step releases the mature human IL-18. The beads were pelleted by centrifugation at 500×g for 5 minutes at 4° C. and washed 5 times with 2 ml ice-cold PBS. The supernatant and all the washing volumes were combined, clarified by centrifugation (14,000×g, 15 min., 4° C.) and concentrated by ultrafiltration (Centricon-10, Amicon). Aliquots of the protein, as well as beads before and after digestion were resolved by 0.1% SDS-12% polyacrylamide gel electrophoresis followed by Coomassie blue staining. A major band of approximately 18 kD, in agreement with the expected mass of mature human IL-18, was obtained in the supernatant. A minor band of 19.5 kD was seen as well (FIG. 5). N-terminal protein sequence analysis of the two bands gave the sequence YFGK . . . , in accordance with that of mature human IL-18. The purified protein was sterilized through a 0.2 µ filter and stored at −70° C.

EXAMPLE 4

Bioassay of Human IL-18

Human IL-18 activity was assessed as described (2). Briefly, spleens of normal C3H/HeJ mice were excised, minced and exposed to Gey buffer (0.144 M NH4Cl in 0.017 M Tris-HCl pH 7.2) to disrupt erythrocytes. The white cells were washed twice with RPMI-5 and then resuspended in RPMI-10. For the preparation of plastic-non-adherent cells, cell suspensions were incubated (60 min., 37° C.) in 100 mm plastic plates (Becton Dickinson Ltd., UK). Non-adherent cells were gently gathered, centrifuged and resuspended in RPMI-10. Viable cells were counted by the trypan blue dye exclusion test and the cell concentration was adjusted to 5×10$^6$ cells/ml. Most of the non-specific esterase-positive cells were removed by these procedures. Suspensions of plastic-non-adherent cells (0.15 ml) were placed in 96-well flat-bottom microtiter culture plate (NUNCLON™, Denmark). Various concentrations of IL-18, polymyxin (1µg/ml) and Con A (0.125 µg/ml) were added to the wells in 50 µl RPMI-10. The plates were incubated for 24 or 48 h at 37° C. in 5% CO2. Following incubation, supernatants were collected and murine IFN-γ titers were determined by ELISA. Incubation of mouse non-adherent spleen cells with human IL-18 alone showed little IFN-γ production, suggesting a requirement for a co-stimulant. Con A alone at 0.125 µg/ml failed to induce significant levels of IFN-γ. When the non-adherent splenocytes were incubated with Con A and the human IL-18 of the present invention, a dose-dependent induction of IFN-γ was obtained (FIG. 6).

EXAMPLE 5

Construction of a Plasmid Coding for Human Pro IL-1β with a Factor Xa Site

PBMC are obtained from peripheral blood of a healthy volunteer by Ficoll-Paque PLUS (Pharmacia) density gradient separation. The PBMC are washed twice with ice-cold PBS containing 2% FBS and resuspended at 2.5×10$^6$ cells/ml in RPMI-1640 medium, supplemented with fetal bovine serum (FBS), 2 mM L-glutamine, 100 U/ml penicillin and 100 U/ml streptomycin (RPMI-10). The culture is stimulated with LPS (1 µg/ml, 3 h, 37° C.). Total RNA is extracted from the cells with the TriPure™ Isolation Reagent (Boehringer Mannheim). One µg total RNA is used for RT-PCR with the Titan one tube RT-PCR kit (Boehringer Mannheim) according to the manufacturer's procedure.

ProIL-1β cDNA is cloned by PCR with sense and reverse primers designed on the basis of the human proIL-1β cDNA (GenBank accession no. M15330). The sense primer corresponds to nucleotides 87–107 of the sequence M15330, preceded by a BamH I cleavage site. The reverse primer corresponds to nucleotides 896–876 of the sequence M15330, preceeded by an Eco RI site. The template is a reverse-transcribed total cellular RNA, isolated from the LPS-stimulated PBMC. The thermocycle conditions are: 10 cycles of 94C, 30 sec; 55° C., 30 sec and 68° C., 2 min followed by 25 cycles of 94° C., 30 sec; 55° C., 30 sec and 68° C., 125 sec/cycle. The resulting 830 bp PCR product is purified by a High Pure™ PCR product purification kit (Boehringer Mannheim) and ligated into the pGEM-T Easy vector to yield plasmid pGEM-proIL-1β. The plasmid is subjected to site-directed mutagenesis with the oligonucleotide ACATGGGATAACGAGGCTATTGAAGGC-CGGGCACCTGTACGA (SEQ ID NO:11), corresponding to nucleotides 405–452 of human IL-1β mRNA and having the mutations Y113I, V114E, H115G and D116R.

The resulting plasmid pGEM-proIL-1β$_{IEGR}$ from a single colony is verified for the presence of a correct insert by restriction enzyme digestion and DNA sequencing. The plasmid is digested with BamH I and EcoR I. The resulting BamH I/EcoR I DNA encoding human proIL-1β$_{IEGR}$ is resolved by electrophoresis in 1.0% agarose and the 0.82 kb band is isolated from the gel by a QIAquick Gel Extraction Kit (DIAGEN, Germany). This DNA is ligated into the pGEX-2TK expression vector (Pharmacia) which is linearized with BamH I and EcoR I. The resulting recombinant plasmid pGEX-proIL-1β$_{IEGR}$ is transformed into E. coli JM109 strain and the resulting vector is confirmed by restriction enzyme digestion and nucleic acid sequencing.

EXAMPLE 6

Expression and Purification of GST-proIL-1β$_{IEGR}$ Fusion Protein

A 50 ml overnight culture from a fresh single colony of E. coli JM109 transformed with plasmid pGEX-proIL-1β$_{IEGR}$ is diluted in 450 ml LB medium containing 100 U/ml ampicillin and grown with shaking at 37° C., until reaching a density of 0.6 OD$_{600}$. Protein expression is then induced by adding IPTG to a final concentration of 0.1 mM and further culturing at 37° C. for 3 h. Bacteria are harvested by centrifugation (5,000×g, 5 min, 4° C.) and rapidly resuspended in a 1:100 starting volume of ice-cold phosphate buffered saline (PBS; 150 mM NaCl, 16 mM Na2HPO4, 4 mM NaH2PO$_4$, pH 7.3), containing the protease inhibitors (leupeptin 1 μg/ml, pepstatin A 1 μg/ml, aprotinin 2 μg/ml, PMSF 0.2 mM and EDTA 5 mM). Cells are lysed on ice by mild sonication (4×15 sec bursts). Triton X-100 is added to a final concentration of 1% and the mixture kept on ice for 5 min. The clarified lysate (14,000×g, 15 min, 4° C.) is mixed with a 50% suspension of glutathione-agarose beads (2 ml. Pharmacia) and the mixture is incubated with mild shaking at 4° C. for 3 h. The beads are pelleted by centrifugation (500×g, 5 min), washed twice with 10 volumes of lysis buffer (1% Triton X-100 in PBS), twice with 10 volumes of 20 mM Tris-HCl, pH 8.0, twice with 10 volumes of 20 mM Tris-HCl, pH 8.0, 150 mM NaCl, and twice with 10 volumes of 20 mM Tris-HCl, pH 8.0, 150 mM NaCl, 2.0 mM CaCl2 (Cleavage Buffer). All steps are carried out at 4° C.

EXAMPLE 7

Cleavage of the Fusion Protein and Purification of Mature Human IL-1β

The glutathione-agarose beads with bound GST-proIL-1β$_{IEGR}$ fusion protein are incubated (6 h, 23° C.) with Factor Xa (New England Biolabs) in 1 ml Cleavage Buffer, using a protease to substrate ratio of 1:50 (w/w), with constant mixing on a rotating wheel. This step releases the mature human IL-1β. The beads are pelleted by centrifugation at 500×g for 5 minutes at 4° C. and washed 5 times with 2 ml ice-cold PBS. The supernatant and all the washes are combined, clarified by centrifugation (14,000×g, 15 min., 4° C.) and concentrated by ultrafiltration (Centricon-10, Amicon). Aliquot of the protein, as well as beads before and after digestion are resolved by 0.1% SDS-12% polyacrylamide gel electrophoresis followed by Coomassie blue staining. A major band of approximately 17 kD, in agreement with the expected mass of mature human IL-1β, is obtained in the supernatant. The purified protein is sterilized through a 0.2 μ filter and stored at −70° C.

EXAMPLE 8

Construction of a Plasmid Coding for Human pro IL-18 with a Caspase-8 Cleavage Site The recombinant plasmid pGEX-proIL-18$_{IEGR}$ of example 1 was modified by inserting a PCR amplified DNA fragment with the caspase-8 cleavage site (LETD). In brief, pGEX-proIL-18$_{IEGR}$ was digested with the restriction enzymes BAM H1 at pos 951 and Hind III at pos 1074 cutting out the DNA portion containing the Pro-domain, the factor Xa cleavage site (IEGR) and three amino acids from the N-terminus of hIL-18.

The same plasmid was used as template for the PCR amplification, by introducing the mutated site LETD on dowstream primer: atgcAAG CTT GCC AAA GTA GTC GGT TTC CAG GTT TTC ATC ATC TTC AGC TAT AA (SEQ ID NO:12). The PCR fragment was purified using the "high pure product purification" kit (Boehringer Mannheim) then similarly cut with BAM HI and Hind III generating a 123 bp insert. The open vector and the insert were separated on Agarose gel and extracted using the commercial kit "Jet Sorb" (Genomed). Ligation was done overnight using a T4 Ligase (New England BioLabs, Beverly Mass., USA) and the ligation products were transformed into E. coli DH5α competent cells. Several colonies were isolated, subcultured and miniprep prepared with the <<Qiagen>> kit. PCR amplification (Perkin Elmer Gene Amp-AmpliTaq DNA polymerase) was done on all the minipreps in order to sequence the essential part of the recombinant plasmid. Final transformation was done in competent bacteria E. Coli JM109 following the TSS Method (Chung, C. T. et al. (1989) Proc. Natl. Acad. Sci. U.S.A. 86, 2172–2175).

EXAMPLE 9

Expression and Purification of GST-proIL-18$_{LETD}$ Fusion Protein

Using the plasmid constructed according to example 8 above, GST-Pro-$_{LETD}$-hIL18 protein expression was achieved in shake flasks and 5 liter fermenters essentially as described in example 2 above.

EXAMPLE 10

Cleavage of the Fusion Protein Using Caspase-8 and Purification of Mature Human IL-18

The glutathione-agarose beads with bound GST-pro-IL-18$_{LETD}$ fusion protein were incubated (4 h, 23° C.) with caspase-8 (Calbiochem) in Cleavage Buffer (defined in example 6) using a protease: substrate ratio of 1:1200 (w/w) with constant mixing on a rotating wheel or roller. The beads were pelleted by centrifugation at 500×g for 5 minutes at 4°

C. and washed 5 times with 2 ml ice-cold PBS. The supernatant and all the washing volumes were combined, clarified by centrifugation (14,000×g, 15 min., 4° C.) and concentrated by centrifugation (Centricon-10, Amicon). The concentrated digest was then submitted to molecular sizing on Superdex-75 (Pharmacia) in order to separate the hIL-18 (18 kDa) from higher molecular weight cleavage products and from the residual proteolytic enzyme (Caspase-8 heterodimer, 29 kDa and hetero-tetramers, 58 kDa).

Caspase-8 enzymatic activity was assayed in the various Superdex-75 fractions using the Caspase-8 Assay kit and the Ac-IETD-AMC fluorogenic substrate (BIOMOL) and was observed in fractions corresponding to a molecular mass of 55 kD (corresponding to the Caspase-8 hetero-tetramer), showing therefore to be very well separated from fractions containing hIL-18 (17 kD).

The highly pure 18 kDa hIL-18 gel filtration fractions were pooled, concentrated on Centricon-10 (Amincon) and finally sterilized through a 0.22 μm filter and stored at −80° C.

Figure 9:
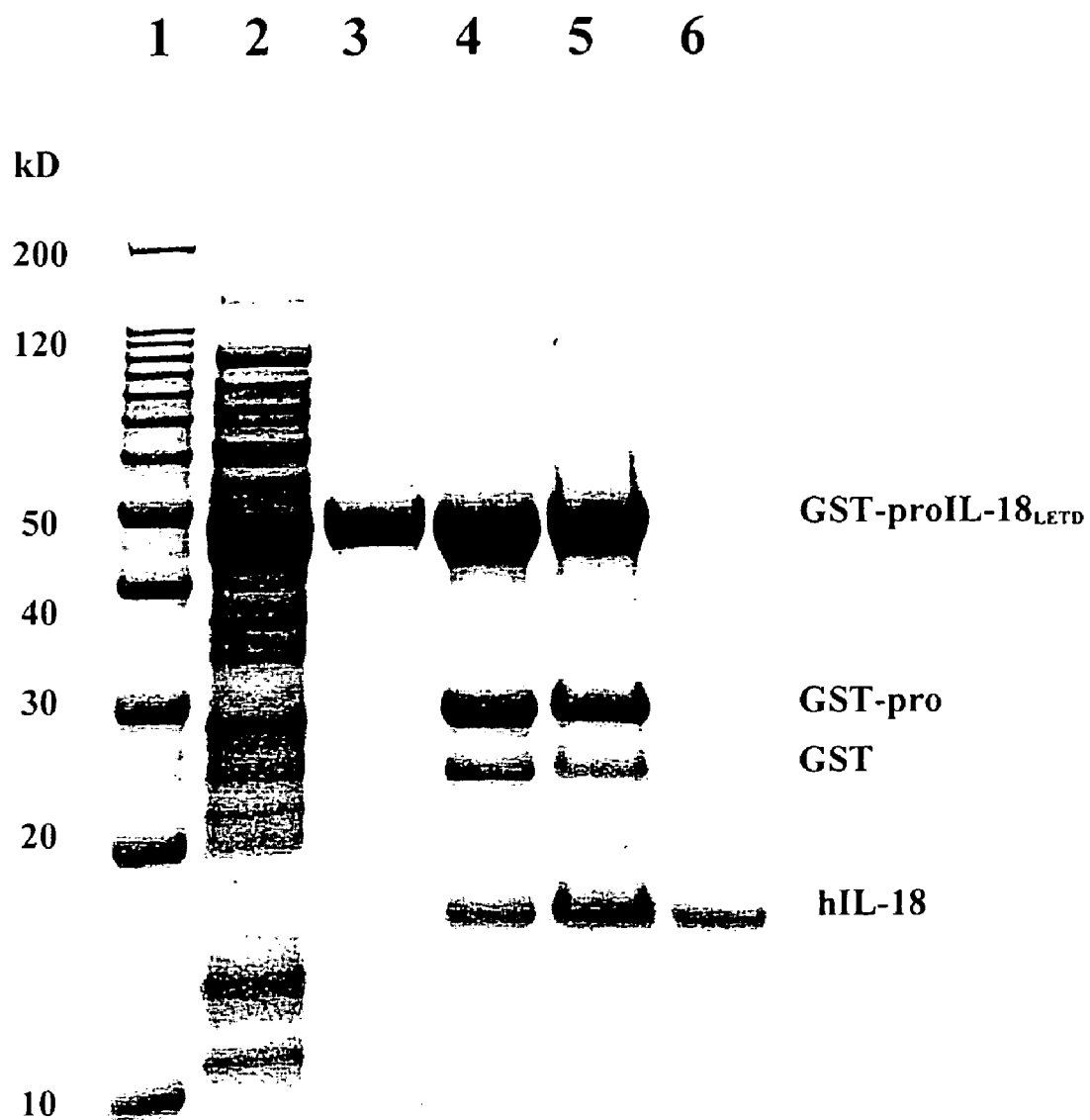
FIG. 9 shows a Coomassie blue stained SDS-PAGE (10% acrylamide gel) of the GST-proIL-18$_{LETD}$ fusion protein purification on glutathione-agarose. Cell break supernatant of recombinant *E. coli* JM109 expressing GST-proIL-18$_{LETD}$ was affinity-purified on glutathione agarose and digested by Caspase-8 on solid phase. The post-digest supernatant was concentrated and applied to molecular sizing on Superdex-75. The lanes are: 1. Molecular mass markers (indicated by kD on the left side); 2. Cell break supernatant; 3. Affinity purified GST-proIL-18$_{LETD}$; 4. Glutathione-agarose resin post Caspase-8 solid phase 4 hr digest; 5. Caspase-8 concentrated 4 hr digest; 6. Superdex-75 pool of pure hIL-18.

Aliquots of the protein, as well as the beads before and after digestion were resolved by 0.1% SDS-12% polyacrylamide gel electrophoresis followed by Coomassie blue staining (FIG. 9). A band of 18 kD, in agreement with the expected mass of mature human IL-18, was observed in the supernatant fraction. Analysis of the bead fraction showed that the cleavage is not complete, since precursor protein remains bound to the beads. Furthermore, some IL-18 cleaved protein remains in the bead fraction.

EXAMPLE 11

Bioassay of Human IL-18 Generated by Caspase-8 Cleavage

Human IL-18 activity was assessed as described (10). Briefly, KG-1 cells were maintained in DMEM containing 20% FBS. For the IL-18 assay, KG-1 cells were suspended at $1.2 \times 10^6$ cells/ml (250 μl/well, 48 well plate) and stimulated with mTNFα (Innogenetics) together with various concentration of hIL-18 (serial dilutions, starting from 80 ng/ml). The plate was incubated 24 h at 37° C. in 5% $CO_2$. Following incubation, supernatants were collected and murine IFN-γ content was determined by ELISA (rec. hIFN-γ and anti-hIFN-γ from R & D Systems).

Human IL-18 induced a dose dependent production of IFN-γ with identical activity to the hIL-18 obtained from the Factor Xa cleavage site construct.

REFERENCES

1. Nakamura, K., Okamura, H., Nagata, K., Komatsu, T., and Tamura, T. (1993) *Infect. Immun.* 61, 64–70
2. Okamura, H., Tsutsui, H., Komatsu, T., Yutsudo, M., Hakura, A., Tanimoto, T., Torigoe, K., Okura, T., Nukada, Y., Hattori, K., Akita, K., Namba, M., Tanabe, F., Konishi, K., Fukuda, S., and Kurimoto, M. (1995) *Nature* 378, 88–91
3. Ushio, S., Namba, M., Okura, T., Hattori, K., Nukada, Y., Akita, K., Tanabe, F., Konishi, K., Micallef, M., Fujii, M., Torigoe, K., Tanimoto, T., Fukuda, S., Ikeda, M., Okamura, H., and Kurimoto, M. (1996) *J. Immunol.* 156, 4274–4279
4. Bazan, J. F., Timans, J. C., and Kaselein, R. A. (1996) *Nature* 379, 591
5. Okamura, H., Nagata, K., Komatsu, T., Tanimoto, T., Nukata, Y., Tanabe, F., Akita, K., Torigoe, K., Okura, T., Fukuda, S., and Kurimoto, M. (1995) *Infect. Immun.* 63, 3966–3972
6. Micallef, M. J., Ohtsuki, T., Kohno, K., Tanabe, F., Ushio, S., Namba, M., Tanimoto, T., Torigoe, K., Fujii, M., Ikeda, M., Fukuda, S., and Kurimoto, M. (1996) *Eur. J. Immunol.* 26, 1647–1651
7. Tsutsui, H., Nakanishi, K., Matsui, K., Higashino, K., Okamura, H., Miyazawa, Y., and Kaneda, K. (1996) *J. Immunol.* 157, 3967–3973
8. Ghayur, T., Banerjee, S., Hugunin, M., Butler, D., Herzog, L., Carter, A., Quintal, L., Sekut, L., Talanian, R., Paskind, M., Wong, W., Kamen, R., Tracey, D., and Allen, H. (1997) *Nature* 386, 619–623
9. Gu, Y., Kuida, K., Tsutsui, H., Ku, G., Hsiao, K., Fleming, M. A., Hayashi, N., Higashino, K., Okamura, H., Nakanishi, K., Kurimoto, M., Tanimoto, T., Flavell, R. A., Sato, V., Harding, M. W., Livingston, D. J., and Su, M. S. (1997) *Science* 275, 206–209
10. Takeda, K., Tsutsui, H., Yoshimoto, T., Adachi, O., Yoshida, N., Kishimoto, T., Okamura, H., Nakanishi. K., and Akira, S. (1998) *Immunity* 8, 383–390
11. Sambrook, J., Fritsch, E. F., and Maniatis, T. (1989) *Molecular Cloning: A Laboratory Manual.,* 2nd edn. Ed., Cold Spring Harbor Laboratories, Cold Spring Harbor, N.Y.
12. Villa, P., Kaufmann, S. H., and Earnshaw, W. C. (1997) Caspases and caspase inhibitors *Trends Biochem. Sci.* 22 388–393
13. Nicholson, D. W., Thornberry, N. A., (1997) Caspases: Killer proteases, *Trends Biochem. Sci.* 22 299–306
14. Garcia-Calvo, M., Peterson, E. P., Rasper, D. M., Vaillancourt, J. P., Zamboni, R., Nicholson, D. W., Thornberry, N. A., (1999) Purification and catalytic properties of human caspase family members, *Cell Death Differ.* 6; (4) 362–369.
15. Konishi, K., Tanabe, F., Taniguchi, M., Yamauchi, H., Tanimoto, T., Ikeda, M., Orita, K., Kurimoto, M. (1997) A simple and sensitive bioassay for the detection of human interleukin-18/interferon-γ inducing factor using human myelomonocytic KG-1 cells, *J. Immunol. Methods* 209 187–191

SEQUENCE LISTING

<160> NUMBER OF SEQ ID NOS: 2

<210> SEQ ID NO 1
<211> LENGTH: 4
<212> TYPE: PRT
<213> ORGANISM: Artificial

-continued

```
<220> FEATURE:
<223> OTHER INFORMATION: Caspase cleavage site.

<400> SEQUENCE: 1

Trp Glu His Asp
1

<210> SEQ ID NO 2
<211> LENGTH: 4
<212> TYPE: PRT
<213> ORGANISM: Artificial
<220> FEATURE:
<223> OTHER INFORMATION: Caspase cleavage site.

<400> SEQUENCE: 2

Leu Glu Thr Asp
1
```

The invention claimed is:

1. A method for the production of a cytokine having a caspase-1 cleavage site from its biologically precursor comprising mutating the caspase-1 cleavage site of the cytokine to a site which is cleaved by a protease other than the caspase-1, the site having the amino acid sequence selected from the group consisting of SEQ ID NOS: 1, 2, 3, 4, 5, 6, or 16 to form a mutated cytokine, and cleaving the mutated cytokine by contact with a protease, other than the caspase-1 protease, that cleaves the site to produce a biologically active cytokine, wherein the cytokine is selected from IL-1β and IL-18.

2. The method according to claim 1, wherein the protease is selected from the group consisting of thrombin, enterokinase, subtilisin, a subtilisin variant, the human rhinovirus 3C protease, Factor Xa protease and caspase-8.

3. The method according to claim 1, wherein said method comprises transfecting a host with a vector comprising a cDNA encoding a precursor of a biologically active molecule mutated an its cleavage site, culturing the transfected host and isolating the cytokine after treatment with a protease.

4. The method according to claim 3, wherein the cDNA is fused in frame to a GST coding sequence and the expressed fusion molecule is captured on glutathione agarose beads prior to treatment with the protease other than the caspase-1 protease.

5. An isolated and purified DNA sequence encoding a cytokine selected from IL-1β or IL-18, wherein the sequence encoding the cytokine native caspase-1 protease cleavage site is substituted by a nucleic acid encoding SEQ ID No: 1, 2, 3, 4, 5, 6, or 16.

6. A method for the production of biologically active human IL-18 comprising the steps of:

a. transfecting a host with a vector comprising a nucleic acid encoding an IL-18 precursor, wherein the nucleic acid has a mutation in the encoded native caspase-1 protease cleavage site whereby the site encodes a site having the amino acid sequence selected from the group consisting of SEQ ID NOS: 1, 2, 3, 4, 5, 6 or 16;

b. culturing the transfected host under conditions sufficient to express the IL-18 precursor;

c. contacting the IL-18 precursor with a protease, other than caspase-1, that, cleaves the precursor; and d. isolating the biologically active human IL-18.

7. The method of claim 6, wherein the nucleic acid encoding the IL-18 precursor is fused in frame to a GST binding protein coding sequence resulting in a fusion protein, wherein the fusion protein is contacted with a ligand or substrate comprising glutathione prior to contact with the protease.

8. The method of claim 7, wherein the ligand or substrate is glutathione beads.

9. The method of claim 6, wherein the other than caspase-1 protease is selected from the group consisting of thrombin, enterokinase, subtilisin, a subtilisin variant, the human rhinovirus 3C protease, Factor Xa protease and caspase-8.

10. The method of claim 6, wherein the host is *E. coli.*

11. The method of claim 10, wherein the nucleic acid encoding the IL-1β precursor is fused in frame to a GST binding protein coding sequence resulting in a fusion protein, wherein the fusion protein is contacted with a ligand or substrate comprising glutathione prior to contact with the protease.

12. The method of claim 11, wherein the ligand or substrate is glutathione beads.

13. A method for the production of biologically active human IL-1β comprising a. transfecting a host with a vector comprising a nucleic acid encoding an IL-1β precursor, wherein the nucleic acid has a mutation in the encoded native caspase-1 protease cleavage site whereby the site encodes a site having the amino acid sequence selected from the group consisting of SEQ ID NOS: 1, 2, 3, 4, 5, 6 or 16;

b. culturing the transfected host under conditions sufficient to express the IL-1β, c. contacting the -1β precursor with a protease other than caspase-1 that cleaves the precursor; and d. isolating the biologically active human IL-1β.

14. The method of claim 13, wherein the protease is selected from the group consisting of thrombin, enterokinase, subtilisin, a subtilisin variant, the human rhinovirus 3C protease, Factor Xa protease and caspase-8.

15. The method of claim 13, wherein the host is *E. coli.*

* * * * *

UNITED STATES PATENT AND TRADEMARK OFFICE
CERTIFICATE OF CORRECTION

| | | |
|---|---|---|
| PATENT NO. | : 7,098,002 B1 | Page 1 of 7 |
| APPLICATION NO. | : 09/958914 | |
| DATED | : August 29, 2006 | |
| INVENTOR(S) | : Menachem Rubinstein et al. | |

It is certified that error appears in the above-identified patent and that said Letters Patent is hereby corrected as shown below:

\*      Column 13 of the Sequence Listing should read

SEQUENCE LISTING

"<110> Rubinstein, Menachem

Liu, Bianling

Novick, Daniela

Dinarello, Charles

Graber, Pierre

<120>  PREPARATION OF BIOLOGICALLY ACTIVE MOLECULES

<130>  057878-000003
<140>         09/958,914
<141>         2001-10-11
<150>  PCT/IL00/00220
<151>  2000-04-13
<150>  129427
<151>  1999-04-13
<160>  14

<170>  PatentIn version 3.1
<210>  1
<211>  6
<212>  PRT
<213>  Artificial Sequence <220>
<223>  A sequence cleaved between the amino acids Arg and Gly by the protease Thrombin

<400>  1

Leu Val Pro Arg Gly Ser
1               5
 <210>  2
 <211>  4

UNITED STATES PATENT AND TRADEMARK OFFICE
CERTIFICATE OF CORRECTION

PATENT NO.       : 7,098,002 B1
APPLICATION NO.  : 09/958914
DATED            : August 29, 2006
INVENTOR(S)      : Menachem Rubinstein et al.

It is certified that error appears in the above-identified patent and that said Letters Patent is hereby corrected as shown below:

<212>  PRT
<213>  Artificial Sequence

<220>
<223>  A sequence cleaved after the Arg residue by the protease factor Xa <400>  2
Ile Gin Giy Arg
1
<210>  3
<211>  4
<212>  PRT
<213>  Artificial Sequence <220>
<223>  A sequence cleaved after the Lys residue by the protease Enterokinase <400>  3

Asp Asp Asp Lys

1
<210>  4
<211>  2
<212>  PRT
<213>  Artificial Sequence <220>
<223>  A sequence cleaved after the Tyr residue by the protease subtilisin <400>  4

His Tyr

1

<210>  5
<211>  2

UNITED STATES PATENT AND TRADEMARK OFFICE
CERTIFICATE OF CORRECTION

PATENT NO. : 7,098,002 B1
APPLICATION NO. : 09/958914
DATED : August 29, 2006
INVENTOR(S) : Menachem Rubinstein et al.

It is certified that error appears in the above-identified patent and that said Letters Patent is hereby corrected as shown below:

<212> PRT
<213> Artificial Sequence

<220>
<223> A sequence cleaved after the Tyr residue by the protease subtilisin

<400> 5

Tyr His

1
<210> 6
<211> 8
<212> PRT
<213> Artificial Sequence

<220>
<223> A sequence cleaved after the Gln residue by the human rhinovirus 3C protease

<400> 6

Leu Glu Val Leu Phe Gln Gly Pro
1               5

<210> 7
<211>    35
<212>    DNA
<213> Homo sapiens

<400> 7
aacatcgaag gtcgttactt tggcaagctt gaatc                    35

<210> 8
<211> 30
<212> DNA
<213> Homo sapiens

<400> 8
cgcgaattcc tagtcttcgt tttgaacat                            30

UNITED STATES PATENT AND TRADEMARK OFFICE
CERTIFICATE OF CORRECTION

PATENT NO. : 7,098,002 B1
APPLICATION NO. : 09/958914
DATED : August 29, 2006
INVENTOR(S) : Menachem Rubinstein et al.

It is certified that error appears in the above-identified patent and that said Letters Patent is hereby corrected as shown below:

<210> 9
<211> 75
<212> DNA
<213> Honto sapiens

<400> 9
tggcaatgaa atttattgac aatacgcttt actttatagc tgaagatgat gaaaacatcg    60
aaggtcgtta ctttg    75

<210> 10
<211> 69
<212> DNA
<213> Homo sapiens

<400> 10
cgtggatcca tggctgctga accagtagaa gacaattgca tcaactttgt ggcaatgaaa    60
tttattgac    69

<210> 11
<211> 42
<212> DNA
<213> Homo sapiens

<400> 11
acatgggata acgaggctat tgaaggccgg gcacctgtac ga    42

<210> 12
<211> 54
<212> DNA
<213> Homo sapiens

<400> 12
atgcaagctt gccaaagtag tcggtttcca ggttttcatc atcttcagct ataa    54

<210> 13
<211> 582
<212> DNA
<213> Homo sapiens

UNITED STATES PATENT AND TRADEMARK OFFICE
CERTIFICATE OF CORRECTION

PATENT NO.        : 7,098,002 B1
APPLICATION NO. : 09/958914
DATED             : August 29, 2006
INVENTOR(S)       : Menachem Rubinstein et al.

It is certified that error appears in the above-identified patent and that said Letters Patent is hereby corrected as shown below:

<400> 13
atggctgctg aaccagtaga agacaattgc atcaactttg tggcaatgaa atttattgac 60
aatacgcttt actttatagc tgaagatgat gaaaacctgg aaaccgacta ctttggcaag 120
cttgaatcta aattatcagt cataagaaat ttgaatgacc aagttctctt cattgaccaa     180
ggaaatcggc ctctatttga agatatgact gattctgact gtagagataa tgcaccccgg 240
accatattta ttataagtat gtataaagat agccagccta gaggtatggc tgtaactatc   300
tctgtgaagt gtgagaaaat ttcaactctc tcctgtgaga acaaaattat ttcctttaag    360
gaaatgaatc ctcctgataa catcaaggat acaaaaagtg acatcatatt ctttcagaga 420
agtgtcccag gacatgataa taagatgcaa tttgaatctt catcatacga aggatacttt   480
ctagcttgtg aaaaagagag agacctttt aaactcattt tgaaaaaaga ggatgaattg 540
ggggatagat ctataatgtt cactgttcaa aacgaagact ag                      582

<210> 14
    <211> 193
    <212> PRT
    <213> Homo sapiens

<400> 14

Met Ala Ala Glu Pro Val Glu Asp Asn Cys Ile Asn Phe Val Ala Met
1               5                   10          •       15

Lys Phe Ile Asp Asn Thr Leu Tyr Phe Ile Ala Glu Asp Asp Glu Asn
        20                  25          •           30

Leu Glu Thr Asp Tyr Phe Gly Lys Leu Glu Ser Lys Leu Ser Val Ile
            35                  40                  45

Arg Asn Leu Asn Asp Gln Val Leu Phe Ile Asp Gln Gly Asn Arg Pro
        50                  55                  60

UNITED STATES PATENT AND TRADEMARK OFFICE
CERTIFICATE OF CORRECTION

PATENT NO. : 7,098,002 B1
APPLICATION NO. : 09/958914
DATED : August 29, 2006
INVENTOR(S) : Menachem Rubinstein et al.

It is certified that error appears in the above-identified patent and that said Letters Patent is hereby corrected as shown below:

Leu Phe Glu Asp Met Thr Asp Ser Asp Cys Arg Asp Asn Ala Pro Arg
   65                  70                  75                  80

Thr Ile Phe Ile Ile Ser Met Tyr Lys Asp Ser Gln Pro Arg Gly Met
                   85                  90                  95

Ala Val Thr Ile Ser Val Lys Cys Glu Lys Ile Ser Thr Leu Ser Cys
              100                 105                 110

Glu Asn Lys Ile Ile Ser Phe Lys Glu Met Asn Pro Pro Asp Asn Ile
         115                 120                 125

Lys Asp Thr Lys Ser Asp Ile Ile Phe Phe Gln Arg Ser Val Pro Gly
         130                 135                 140

His Asp Asn Lys Met Gln Phe Glu Ser Ser Ser Tyr Glu Gly Tyr Phe
 145                 150                 155                 160

Leu Ala Cys Glu Lys Glu Arg Asp Leu Phe Lys Leu Ile Leu Lys Lys
              165                 170                 175

Glu Asp Glu Leu Gly Asp Arg Ser Ile Met Phe Thr Val Gln Asn Glu
              180                 185                 190

Asp"

<160> SEQ ID NO 15
<210> Length: 4
<211> TYPE: PRT
<213> ORGANISM: Artificial
<220> FEATURE:
<223> OTHER INFORMATION: Caspase cleaveage site.

<400> SEQUENCE: 15

Trp Glu His Asp
1

<210> SEQ ID NO 16
<211> Length: 4

UNITED STATES PATENT AND TRADEMARK OFFICE
CERTIFICATE OF CORRECTION

| | |
|---|---|
| PATENT NO. | : 7,098,002 B1 |
| APPLICATION NO. | : 09/958914 |
| DATED | : August 29, 2006 |
| INVENTOR(S) | : Menachem Rubinstein et al. |

It is certified that error appears in the above-identified patent and that said Letters Patent is hereby corrected as shown below:

<212> TYPE: PRT
<213> ORGANISM: Artificial
<220> FEATURE:
<223> OTHER INFORMATION: Caspase cleavage site.

<400> SEQUENCE: 16

Leu Glu Thr Asp

\*    In the Claims, Claim 10, Column 16, line 39 "The method of claim 10" should read --The method of claim 13--.

Signed and Sealed this

Twenty-sixth Day of December, 2006

JON W. DUDAS
*Director of the United States Patent and Trademark Office*